United States Patent [19]

Kim et al.

[11] Patent Number: 5,077,423

[45] Date of Patent: Dec. 31, 1991

[54] S-(N-ALKOXYCARBONYL, N-SUBSTITUTED)AMINOMETHYL ISOTHIOUREA DERIVATIVE

[75] Inventors: Dae-Whang Kim; Sung-Yeap Hong; Jae-Wook Ryu; Jae-Chun Woo, all of Daejeon, Rep. of Korea

[73] Assignee: Korea Research Institute of Chemical Technology, Seoul, Rep. of Korea

[21] Appl. No.: 391,102

[22] Filed: Aug. 8, 1989

[30] Foreign Application Priority Data

Sep. 3, 1988 [KR] Rep. of Korea .............. 11395/1988

[51] Int. Cl.$^5$ ........................................... C07C 335/32
[52] U.S. Cl. ........................................ 558/5; 540/553; 544/8; 544/67; 544/315; 546/300; 546/305; 546/331; 548/351; 548/565; 549/470

[58] Field of Search .................... 558/5; 549/462, 470; 546/300, 305, 331; 540/553; 544/8, 67, 315; 548/351, 565

[56] References Cited

U.S. PATENT DOCUMENTS 2,302,885 11/1942 Orthner et al. .......................... 558/5
2,411,655 11/1946 Graenacher et al. ................... 558/5

Primary Examiner—Bernard Dentz
Attorney, Agent, or Firm—Merchant, Gould, Smith, Edell, Welter & Schmidt

[57] ABSTRACT

S-(N-alkoxycarbonyl, N-substituted)amino methyl isothiourea derivative, which is a useful intermediate for the production of 1,3,5-thiadiazine-4-one derivative, is disclosed. The above compound can be produced by reacting the carbamate compound of the formula(II) with the thiourea compound of the formula(III).

15 Claims, No Drawings

S-(N-ALKOXYCARBONYL, N-SUBSTITUTED)AMINOMETHYL ISOTHIOUREA DERIVATIVE

BACKGROUND OF THE INVENTION

Field of the Invention

The present invention relates to the novel S-(N-alkoxycarbonyl, N-substituted)amino methyl isothiourea derivative of formula (I)

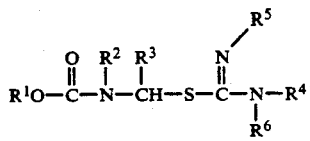

wherein each of $R^1$, $R^2$, $R^3$, $R^4$, $R^5$ and $R^6$, which may be the same or different, represents an alkyl group, an alkenyl group, an alkynyl group, a haloalkyl group, a haloalkenyl group, a haloalkynyl group, an alkoxyalkyl group, a cycloalkyl group, a cycloalkenyl group, an aryl group, a substituted-aryl group, an aralkyl group, a substituted-aralkyl group, a naphthyl, a pyridyl,

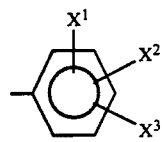

(wherein each of $X^1$, $X^2$ and $X^3$, which may be the same of different, represents a hydrogen atom, an alkyl group, a cycloalkyl group, an alkoxy group, an acetyl, a haloalkyl group, a halogen atom, $CF_3$, $NO_2$, hydroxy, a benzyl group, a phenyl group, a phenoxy group, a phenylthio group, a benzyl- or halogen-substituted benzyl, phenyl, phenoxy or phenylthio group) or

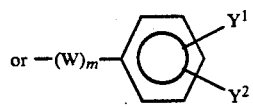

(wherein each of $Y^1$ and $Y^2$, which may be the same or different, represents a hydrogen atom, a lower alkyl group, a halogen atom, $CF_3$, a lower alkoxy group, W represents a

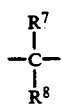

group, (in which each of $R^7$ and $R^8$ represents a hydrogen atom or a lower alkyl group), —O— group, a

group, or a —OCH$_2$— group, and m represents an integer of 0 or 2), and each of $R^2$, $R^3$, $R^4$, $R^5$ and $R^6$ may be a hydrogen atom. And $R^4$ and $R^5$, or $R^4$ and $R^6$ forms together with —(CH$_2$)$_n$— (wherein n is an integer of 2 to 4), —CH$_2$—O—CH$_2$— or —CH$_2$—S—CH$_2$—; provided, however, that at least one of $R^4$, $R^5$ and $R^6$ is a hydrogen atom.

DESCRIPTION OF THE BACKGROUND

The compound of the formula (I) is a useful intermediate for the production of 1,3,5-thiadiazine-4-one, 2-imino-1,3,5-thiadiazine-4-one, imidazo- and pyrimido-1,3,5-thiadiazine-4-one, 5-phenoxy-phenyl-tetrahydro-1,3,5-thiadiazine-4-one, dihydro-1,3,5-thiadiazine-4-one and derivatives thereof, etc.

In the conventional methods for preparing the 1,3,5-thiadiazine-4-one derivatives, the end products have been prepared by reacting N-chloromethyl carbamoyl chloride with thiourea. In these methods, N-chloromethyl carbamoyl chloride is too reactive and very inconvenient in treatment due to its instability. Furthermore, there are many drawbacks to the conventional methods. For example, phosgene, which is very poisonous, is used for the production of N-chloromethyl carbamoyl chloride. Moreover, many isomeric compounds form when unsymmetric thiourea, which has different substituents, is a reactant, thereby resulting in poor product yield and a more complicated process especially with respect to product isolation.

SUMMARY OF THE INVENTION

The present inventors engaged in research in order to solve the above problems/disadvantages and concluded that 1,3,5-thiadiazine-4-one derivatives can be easily prepared with a high yield by cyclization in the presence, or in the absence of solvent of S-(N-alkoxycarbonyl, N-substituted)amino methyl isothiourea derivative of the present invention.

DETAILED DESCRIPTION OF THE PRESENT INVENTION

The present invention provides the compound of the formula (I) and the process thereof which comprises reacting the compound of formula (II) with thiourea of formula (III).

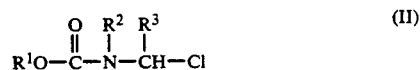 (II)

 (III)

In the above formulas, $R^1$, $R^2$, $R^3$, $R^4$, $R^5$ and $R^6$ are as defined above.

The compound of formula (I) according to the present invention can be prepared by reacting the compound of formula (II) with the compound of formula (III) in the presence or in the absence of a base within a temperature range of from −20° C. to 120° C. It is preferable, however, to proceed the reaction within a temperature range of 10° to 60° C.

The compound of formula (I), in which the radical $R^6$ is a hydrogen atom, has tautomeric structures as follows:

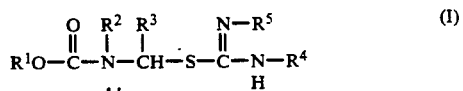 (I)

-continued

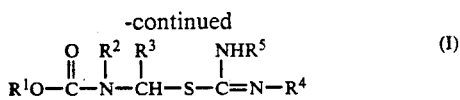
(I)

The compound of formula (I) can be obtained in the form of a base or acid addition salt, if necessary. When a base is not added during the reaction, the product is obtained in the form of the salt, and when a base is added, it is obtained in the form of a free salt of isothiourea. When the acid is added to a free salt the product is obtained as the form of an acid addition salt thereof.

The reaction of the invention is preferably proceeded in the solvent which does not severely affect the reaction. Here, as the solvent, there may be employed water, an aliphatic hydrocarbon solvent such as hexane, cyclohexane, an aromatic hydrocarbon solvent such as benzene, toluene, xylene or chlorobenzene, a ketone solvent such as acetone, cyclohexanone, methylethyl ketone or methylisobutyl ketone, an ether solvent such as ethyl ether, isopropyl ether, dioxane or tetrahydrofuran, a halogenated hydrocarbon solvent such as methylene chloride, chloroform, tetrachloromethane, dichloroethane or trichloroethylene, an aliphatic ester solvent such as ethyl acetate, an aliphatic amide solvent such as acetonitrile, nitromethane, nitropropane, dimethylformamide or dimethylacetamide, an alcohol solvent such as ethanol, isopropanol or tert.-butanol, and dimethyl sulfoxide, etc. The above solvent may be used solely or in combination with water and/or other organic solvent solvents. However, the solvent is not restricted to such specific examples.

As the base, there may be employed an inorganic base such as potassium hydroxide, sodium hydroxide, aqueous ammonia, potassium carbonate, sodium carbonate, sodium bicarbonate, sodium phosphate, sodium biphosphate, borax, calcium hydroxide or calcium oxide, etc., or an organic base such as triethylamine, pyridine, 1,8-diazabicyclo[5,4,0,7]-undecene or triethylene-diamine, etc. These bases can be used in the form of powder or solution. The molar ratio of the reactant to starting material in the reaction is 1:1 which is stoichiometric amount. However, an excess amount of anyone can be used, unless the reaction is affected. The amount of the base can be one equivalent molar ratio to the reactants. An excess amount of the base does not harm the reaction. The amount of the solvent is not restricted. That is to say, an excess amount thereof may be used, and also only a small amount enough to agitate the reactants may be used. After the completion of the reaction, the compound of formula (I) is extracted from the reaction mixture by treating the appropriate solvent, washing, drying, and distilling the solvent, or if necessary, the conventional recrystallization or purification can be employed.

When the compound of the formula (I) is required to be obtained in the form of the salt thereof, the product is subjected to treatment with an appropriate acid. As an acid for preparing the salt thereof, there may be employed an inorganic acid or organic acid such as hydrochloric acid, hydrobromic, sulfuric acid, phosphoric acid, nitric acid, perchloric acid, acetic acid, formic acid, trichloroacetic acid, benzenesulfonic acid, toluene sulfonic acid, etc.

The typical compound of the formula (I) is shown in Table I.

| No. | R¹ | R² | R³ | R⁴ | R⁵ | R⁶ | property |
|---|---|---|---|---|---|---|---|
| 1 | —CH₃ | Ph | H | i-C₃H₇ | t-C₄H₉ | H | liquid |
| 2 | —C₂H₅ | Ph | H | " | " | H | |
| 3 | —C₃H₇ | Ph | H | " | " | H | |
| 4 | -i-C₃H₇ | Ph | H | " | " | H | |
| 5 | -n-Bu | Ph | H | " | " | H | |
| 6 | -s-Bu | Ph | H | " | " | H | |
| 7 | -t-Bu | Ph | H | " | " | H | |
| 8 | -cyclohexyl | Ph | H | " | " | H | |
| 9 | —CH₂Ph | Ph | H | " | " | H | liquid |
| 10 | —CH₃ | (2,2-dimethylindane) | H | " | " | H | liquid |
| 11 | —Ph | Ph | H | " | " | H | liquid |
| 12 | (4-Cl-C₆H₄)- | Ph | H | " | " | H | mp. 95~97° C. |
| 13 | (2-Cl-C₆H₄)- | Ph | H | " | " | H | |
| 14 | (2,4-Cl₂-C₆H₃)- | Ph | H | " | " | H | |
| 15 | (4-Br-C₆H₄)- | Ph | H | " | " | H | mp. 76~78° C. |
| 16 | (4-NO₂-C₆H₄)- | Ph | H | " | " | H | mp. 105~106° C. |

-continued

| No. | R¹ | R² | R³ | R⁴ | R⁵ | R⁶ | property |
|---|---|---|---|---|---|---|---|
| 17 | 4-CF₃-C₆H₄- | Ph | H | " | " | H | |
| 18 | 5,6,7,8-tetrahydronaphthalen-1-yl (8-methyl) | Ph | H | i-C₃H₇ | t-C₄H₉ | H | mp. 106~108° C. |
| 19 | 2,2-dimethyl-2,3-dihydrobenzofuran-7-yl | " | H | " | " | H | liquid |
| 20 | | t-Bu | H | CH₃ | | | |
| 21 | | CH₃ | Ph | i-C₃H₇ | | | |
| 22 | | C₂H₅ | H | CH₃ | | | |
| 23 | | C₂H₅ | H | i-C₃H₇ | i-C₃H₇ | H | |
|  |  |  |  |  | t-C₄H₉ | H | |
|  |  |  |  |  | i-C₃H₇ | H | |
| 24 | 4-NO₂-C₆H₄- (2-methyl) | CH₂CH=CH₂ | H | CH₃ | CH₃ | H | |
| 25 |  | CH₂CH=CH₂ | H | CH₃ | i-C₃H₇ | H | |
| 26 | 4-NO₂-C₆H₄- (2-methyl) | i-C₃H₇ | H | CH₃ | CH₃ | H | |
| 27 | C₆H₅-CH₂- | i-C₃H₇ | H | CH₃ | i-C₃H₇ | H | |

-continued

| No. | R¹ | R² | R³ | R⁴ | R⁵ | R⁶ | property |
|---|---|---|---|---|---|---|---|
| 28 | 4-Cl-C₆H₄ | i-C₃H₇ | H | C₂H₅ | C₂H₅ | H | |
| 29 | CH₃ | n-C₄H₉ | H | CH₃ | i-C₃H₇ | H | |
| 30 | Me | i-C₄H₉ | H | i-C₃H₇ | i-C₃H₇ | H | |
| 31 | —Ph—NO₂ | S—C₄H₉ | H | CH₃ | i-C₃H₇ | H | |
| 32 | —Ph—NO₂ | t-C₄H₉ | H | CH₃ | n-C₃H₇ | H | |
| 33 | " | Ph | H | 3-F-C₆H₄-CH₂— | t-C₄H₉ | H | |
| 34 | —PhNO₂ | Ph | H | 4-CH₃-C₆H₄-CH₂— | t-C₄H₉ | H | |
| 35 | —PhNO₂ | Ph | H | 4-Br-C₆H₄-CH₂— | " | H | |
| 36 | —PhNO₂ | Ph | H | 4-Cl-C₆H₄-CH₂— | " | H | |
| 37 | —PhNO₂ | Ph | H | 3,4-Cl₂-C₆H₃-CH₂— | " | H | |
| 38 | —CH₂Ph | Ph | H | 2,4-Cl₂-C₆H₃-CH₂— | " | H | |

-continued

| No. | R¹ | R² | R³ | R⁴ | R⁵ | R⁶ | property |
|---|---|---|---|---|---|---|---|
| 39 | —C₆H₄—NO₂ | Ph | H | 4-Cl-C₆H₄-CH(CH₃)₂ | " | H | |
| 40 | " | Ph | H | 4-t-Bu-C₆H₄-CH₂ | " | H | |
| 41 | " | Ph | H | " | CH₃ | H | |
| 42 | " | i-C₃H₇ | H | Ph | CH₃ | H | |
| 43 | " | " | H | 4-Cl-3-CH₃-C₆H₃ | CH₃ | H | |
| 44 | " | t-C₄H₉ | H | Ph | CH₃ | H | |
| 45 | " | " | H | Ph | i-C₃H₇ | H | |
| 46 | " | " | H | 4-Cl-3-CH₃-C₆H₃ | C₂H₅ | H | |
| 47 | " | " | H | 4-Cl-3-Me-C₆H₃ | CH₃ | H | |
| 48 | —C₆H₄—NO₂ | t-C₄H₉ | H | 2,3-diCl-C₆H₃ | CH₃ | H | |

-continued

| No. | R¹ | R² | R³ | R⁴ | R⁵ | R⁶ | property |
|---|---|---|---|---|---|---|---|
| 49 | " | —CH₂Ph | H | 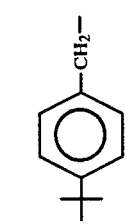 | i-C₃H₇ | H | |
| 50 | Me | t-C₈H₁₇ | | Ph | CH₃ | H | |
| 51 | Et | Ph | H | CH₃ | H | H | |
| 52 | Ph | Ph | H | C₂H₅ | 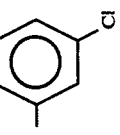 | H | |
| 53 | —PhNO₂ | Ph | H | " | i-C₃H₇ | H | |
| 54 | —PhNO₂ | Ph | H | " | t-C₄H₉ | H | |
| 55 | —CH₃ | Ph | H | n-C₃H₇ | n-C₃H₇ | H | |
| 56 | —PhNO₂ | Ph | H | CH₂CH=CH₂ | CH₂CH=CH₂ | H | |
| 57 | —PhNO₂ | Ph | H | " | n-C₃H₇ | H | |
| 58 | —PhNO₂ | Ph | H | " | i-C₃H₇ | H | |
| 59 | —PhNO₂ | Ph | H | " | s-C₃H₇ | H | |
| 60 | —PhNO₂ | Ph | H | " | i-C₃H₇ | H | |
| 61 | —PhNO₂ | Ph | H | i-C₃H₇ | i-C₃H₇ | H | |
| 62 | —PhNO₂ | Ph | H | i-C₄H₉ | i-C₄H₉ | H | |
| 63 | —PhNO₂ | Ph | H | " | i-C₃H₇ | H | |
| 64 | —PhNO₂ | Ph | H | " | t-C₄H₉ | H | |
| 65 | —PhNO₂ | Ph | H | s-C₄H₉ | s-C₄H₉ | H | |
| 66 | —PhNO₂ | Ph | H | i-C₃H₇ | t-C₄H₉ | H | |
| 67 | —PhNO₂ | Ph | H | CH₂Ph | t-C₈H₁₇ | H | |
| 68 | —PhNO₂ | Ph | H | Ph | i-C₃H₇ | H | |
| 69 | —PhNO₂ | Ph | H | CH₃ | C₂H₅ | H | |
| 70 | —PhNO₂ | 4-Cl—Ph | H | i-C₃H₇ | CH₃ | H | |
| 71 | —PhNO₂ | 4-Cl—Ph | H | " | i-C₃H₇ | H | |
| 72 | —PhNO₂ | 4-Cl—Ph | H | " | t-C₄H₉ | H | |
| 73 | —PhNO₂ | 4-Cl—Ph | H | s-C₄H₉ | s-C₄H₉ | H | |
| 74 | —PhNO₂ | 4-Cl—Ph | H | " | t-C₄H₉ | H | |
| 75 | —PhNO₂ | 3-Cl—Ph | H | CH₃ | CH₃ | H | |
| 76 | —PhNO₂ | 3-Cl—Ph | H | C₂H₅ | t-C₄H₉ | H | |
| 77 | —PhNO₂ | 3-Cl—Ph | H | CH₂CH=CH₂ | i-C₃H₇ | H | |
| 78 | —PhNO₂ | 3-Cl—Ph | H | " | t-C₄H₉ | H | |
| 79 | —PhNO₂ | 3-Cl—Ph | H | " | —CH₂Ph | H | |
| 80 | —PhNO₂ | 3-Cl—Ph | H | i-C₃H₇ | i-C₃H₇ | H | |
| 81 | —PhNO₂ | 3-Cl—Ph | H | " | t-C₄H₉ | H | |
| 82 | —PhNO₂ | 3-Cl—Ph | H | t-C₄H₉ | t-C₈H₁₇ | H | |
| 83 | —PhNO₂ | 3-Cl—Ph | H | " | t-C₄H₉ | H | |
| 84 | —PhNO₂ | 3-Cl—Ph | H | s-C₄H₉ | s-C₄H₉ | H | |
| 85 | —PhNO₂ | 3-Cl—Ph | H | " | t-C₄H₉ | H | |

-continued

| No. | R¹ | R² | R³ | R⁴ | R⁵ | R⁶ | property |
|---|---|---|---|---|---|---|---|
| 86 | —PhNO₂ | 3-Cl—Ph | H | CH₃OC₃H₈ | i-C₃H₇ | H | |
| 87 | —PhNO₂ | 3-Cl—Ph | H | CH₃OC₂H₄ | t-C₄H₉ | H | |
| 88 | —PhNO₂ | 3-Cl—Ph | H | ⟨cyclopentyl-H⟩ | i-C₃H₇ | H | |
| 89 | —PhNO₂ | 3-Cl—Ph | H | n-C₆H₁₃ | " | | |
| 90 | —PhNO₂ | 3-Cl—Ph | H | —CH—Ph | " | | |
| 91 | —PhNO₂ | 2-Cl—Ph | H | C₂H₅ | t-C₄H₉ | H | |
| 92 | —PhNO₂ | 2-Cl—Ph | H | CH₂CH=CH₂ | i-C₃H₇ | H | |
| 93 | —PhNO₂ | 2-Cl—Ph | H | " | t-C₄H₉ | H | |
| 94 | —PhNO₂ | 2-Cl—Ph | H | i-C₃H₇ | i-C₃H₇ | H | |
| 95 | —PhNO₂ | 2-Cl—Ph | H | " | t-C₄H₉ | H | |
| 96 | —PhNO₂ | 2-Cl—Ph | H | s-C₄H₉ | s-C₄H₉ | H | |
| 97 | —PhNO₂ | 2-Cl—Ph | H | " | t-C₄H₉ | H | |
| 98 | —PhNO₂ | 2-Cl—Ph | H | i-C₃H₇ | ⟨cyclopentyl-H⟩ | | |
| 99 | —PhNO₂ | 2-Cl—Ph | H | —CH₂— | i-C₃H₇ | H | |
| 100 | —PhNO₂ | 2-Cl—Ph | H | CH₃OCH₂CH₂CH₂ (epoxide) | t-C₄H₉ | H | |
| 101 | —PhNO₂ | 3-CF₃—Ph | H | s-C₄H₉ | t-C₄H₉ | H | |
| 102 | —PhNO₂ | 4-F—Ph | H | H | i-C₃H₇ | H | |
| 103 | —PhNO₂ | 4-F—Ph | H | H | t-C₄H₉ | H | |
| 104 | —PhNO₂ | 4-F—Ph | H | C₂H₅ | " | H | |
| 105 | —PhNO₂ | 4-F—Ph | H | i-C₃H₇ | t-C₄H₉ | H | |
| 106 | —PhNO₂ | 4-F—Ph | H | " | " | H | |
| 107 | —PhNO₂ | 4-F—Ph | H | s-C₄H₉ | " | H | |
| 108 | —PhNO₂ | 4-F—Ph | H | " | CH₂CH=CH₂ | H | |
| 109 | —PhNO₂ | 4-Br—Ph | H | CH₃ | CH₃ | H | |
| 110 | —PhNO₂ | 4-Br—Ph | H | CH₃ | i-C₃H₇ | H | |
| 111 | —PhNO₂ | 4-Br—Ph | H | i-C₃H₇ | t-C₄H₉ | H | |
| 112 | —PhNO₂ | 4-Br—Ph | H | " | " | H | |
| 113 | —PhNO₂ | 4-Br—Ph | H | s-C₄H₉ | i-C₃H₇ | H | |
| 114 | —PhNO₂ | 2-CH₃Ph | H | CH₃ | t-C₄H₉ | H | |
| 115 | —PhNO₂ | " | H | C₂H₅ | i-C₃H₇ | H | |
| 116 | —PhNO₂ | " | H | CH₂CH=CH₂ | t-C₄H₉ | H | |
| 117 | —PhNO₂ | " | H | i-C₃H₇ | i-C₃H₇ | H | |
| 118 | —PhNO₂ | " | H | " | t-C₄H₉ | H | |
| 119 | —PhNO₂ | " | H | s-C₄H₉ | t-C₄H₉ | H | |
| 120 | —PhNO₂ | " | H | n-C₆H₁₃ | i-C₃H₇ | H | |

5,077,423

-continued

| No. | R¹ | R² | R³ | R⁴ | R⁵ | R⁶ | property |
|---|---|---|---|---|---|---|---|
| 121 | —PhNO₂ | " | H | i-C₃H₇ | 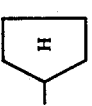 H | H | |
| 122 | —PhNO₂ | 4-CH₃—Ph | H | C₂H₅ | t-C₄H₉ | H | |
| 123 | —PhNO₂ | " | H | n-C₃H₇ | i-C₃H₇ | H | |
| 124 | —PhNO₂ | 4CH₃—Ph | H | CH₂CH=CH₂ | i-C₃H₇ | H | |
| 125 | —PhNO₂ | " | H | i-C₃H₇ | i-C₃H₇ | H | |
| 126 | —PhNO₂ | " | H | n-C₃H₇ | t-C₄H₉ | H | |
| 127 | —PhNO₂ | " | H | i-C₃H₇ | t-C₄H₉ | H | |
| 128 | —PhNO₂ | " | H | s-C₄H₉ | t-C₄H₉ | H | |
| 129 | —PhNO₂ | " | H | —CH₂Ph | i-C₃H₇ | H | |
| 130 | —PhNO₂ | -3CH₃Ph | H | C₂H₅ | C₂H₅ | H | |
| 131 | —PhNO₂ | " | H | i-C₃H₇ | i-C₃H₇ | H | |
| 132 | —PhNO₂ | " | H | i-C₃H₇ | t-C₄H₉ | H | |
| 133 | —PhNO₂ | " | H | s-C₄H₉ | s-C₄H₉ | H | |
| 134 | —PhNO₂ | 4C₂H₅Ph | H | i-C₃H₇ | t-C₄H₉ | H | |
| 135 | —PhNO₂ | " | H | s-C₅H₉ | t-C₄H₉ | H | |
| 136 | —PhNO₂ | 2C₂H₅Ph | H | CH₂CH=CH₂ | t-C₄H₉ | H | |
| 137 | —PhNO₂ | " | H | i-C₃H₇ | i-C₃H₇ | H | |
| 138 | —PhNO₂ | " | H | " | t-C₄H₉ | H | |
| 139 | —PhNO₂ | 2-i-C₃H₇Ph | H | s-C₄H₉ | t-C₄H₉ | H | |
| 140 | —PhNO₂ | 2-i-C₃H₇Ph | H | i-C₃H₇ | i-C₃H₇ | H | |
| 141 | —PhNO₂ | 4-CH₃OPh | H | s-C₄H₉ | t-C₄H₉ | H | |
| 142 | —PhNO₂ | " | H | CH₂CH=CH₂ | i-C₃H₇ | H | |
| 143 | —PhNO₂ | " | H | n-C₃H₇ | t-C₄H₉ | H | |
| 144 | —PhNO₂ | " | H | i-C₃H₇ | i-C₃H₇ | H | |
| 145 | —PhNO₂ | " | H | " | t-C₄H₉ | H | |
| 146 | —PhNO₂ | " | H | " | " | H | |
| 147 | —PhNO₂ | " | H | " | t-C₄H₉ | H | |
| 148 | —PhNO₂ | " | H | n-C₃H₇ |  H | H | |
| 149 | —PhNO₂ | 2-CH₃OPh | H | s-C₄H₉ | t-C₄H₉ | H | |
| 150 | —PhNO₂ | 4-NO₂Ph | H | i-C₃H₇ | i-C₃H₇ | H | |
| 151 | —PhNO₂ | 2,4(CH₃)₂Ph | H | CH₃ | H | H | |
| 152 | —PhNO₂ | " | H | i-C₃H₇ | i-C₃H₇ | H | |
| 153 | —PhNO₂ | " | H | " | " | H | |
| 154 | —PhNO₂ | " | H | " | t-C₄H₉ | H | |
| 155 | —PhNO₂ | 2,4(CH₃)₂Ph | H | s-C₄H₉ | i-C₃H₇ | H | |
| 156 | —PhNO₂ | " | H | i-C₃H₇ | t-C₄H₉ | H | |
| 157 | —PhNO₂ | " | H | s-C₄H₉ | " | H | |
| 158 | —PhNO₂ | 2CH₃,4ClPh | H | s-C₄H₉ | t-C₄H₉ | H | |
| 159 | —PhNO₂ | " | H | i-C₃H₇ | " | H | |

-continued

| No. | R¹ | R² | R³ | R⁴ | R⁵ | R⁶ | property |
|---|---|---|---|---|---|---|---|
| 160 | —PhNO₂ | 2,6(CH₃)₂Ph | H | " | i-C₃H₇ | H | |
| 161 | —PhNO₂ | 2,6Et₂Ph | H | " | i-C₃H₇ | H | |
| 162 | —PhNO₂ | 2,4Cl₂Ph | H | i-C₃H₇ | t-C₄H₉ | H | |
| 163 | —PhNO₂ | " | H | s-C₄H₉ | s-C₄H₉ | H | |
| 164 | —PhNO₂ | " | H | " | t-C₄H₉ | H | |
| 165 | —PhNO₂ | 3,5Cl₂Ph | H | i-C₃H₇ | t-C₄H₉ | H | |
| 166 | —PhNO₂ | " | H | CH₂CH=CH₂ | i-C H | H | |
| 167 | —PhNO₂ | " | H | " | t-C₃H₇ | H | |
| 168 | —PhNO₂ | " | H | " | t-C₄H₉ | H | |
| 169 | —PhNO₂ | 2,5Cl₂Ph | H | s-C₃H₇ | " | H | |
| 170 | —PhNO₂ | Ph | H | —CH₂—CH₂— | | H | |
| 171 | —PhNO₂ | " | H | —CH₂CH₂CH₂— | | H | |
| 172 | —PhNO₂ | 2ClPh | H | —CH₂CH₂— | | H | |
| 173 | —PhNO₂ | 4ClPh | H | —CH₂CH₂— | | H | |
| 174 | —PhNO₂ | " | H | —CH(CH₃)—CH₂— | | H | |
| 175 | —PhNO₂ | 4FPh | H | —CH₂CH₂— | | H | |
| 176 | —PhNO₂ | " | H | —CH(CH₃)—CH₂— | | H | |
| 177 | —PhNO₂ | 2,3,6-Me₃Ph | H | —CH₂CH₂— | | H | |
| 178 | —PhNO₂ | p-PhCH(2-Me,6-Me)O—Ph | H | i-C₃H₇ | t-C₄H₉ | H | |
| 179 | —PhNO₂ | (2,6-Me₂-4-(4-CH₃Ph-O)Ph) | H | i-C₃H₇ | t-C₄H₉ | | |
| 180 | —PhNO₂ | (2,6-Me₂-4-(2-Me-4-CH₃Ph-O)Ph) | H | i-C₃H₇ | | | |
| 181 | —PhNO₂ | | | i-C₃H₇ | i-C₃H₇ | | |

-continued
| No. | R¹ | R² | R³ | R⁴ | R⁵ | R⁶ | property |
|---|---|---|---|---|---|---|---|
| 182 | —PhNO₂ | 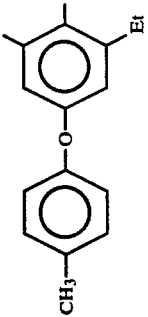 | H | i-C₃H₇ | i-C₃H₇ | | |
| 183 | —PhNO₂ | 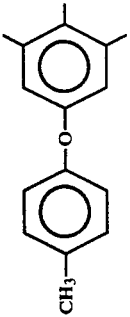 | H | i-C₃H₇ | i-C₄H₉ | | |
| 184 | —PhNO₂ | 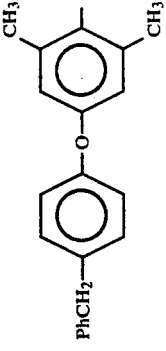 | H | i-C₃H₇ | i-C₃H₇ | | |
| 185 | —Ph | Ph | H | H | t-Bu | H | |
| 186 | —Ph | Ph | H | H | t-Bu | CH | |
| 187 | —Ph | CH₂=CHCH₂ | H | H | CH₃ | | |
| 188 | —PhNO₂ | CH₃ | —Ph | i-C₃H₇ | t-Bu | H | |
| | | | | t-Bu | | | |
| 189 | —PhNO₂ | " | —Ph | CH₃ | C₂H₅ | H | |
| 190 | —PhNO₂ | " | —PhCl | CH₃ | CH₃ | H | |
| 191 | —PhNO₂ | CH₃ | —PhCl | CH₃ | i-C₃H₇ | H | |
| 192 | —PhNO₂ | CH₃ | —PhOCH | CH₃ | i-C₃H₇ | H | |
| 193 | —PhNO₂ | CH₂=CHCH₂ | Ph | CH₃ | CH₃ | H | |
| 194 | —PhNO₂ | PhCH | PhCl | CH₃ | CH₃ | H | |
| 195 | —Ph | PhCl | H. | H | CH₃ | CH₃ | |

-continued

| No. | R¹ | R² | R³ | R⁴ | R⁵ | R⁶ | property |
|---|---|---|---|---|---|---|---|
| 196 | —Ph | t-C₄H₉ | H | H | CH₃ | 3,5-dimethylphenyl | |
| 197 | —Ph | t-C₄H₉ | H | H | CH₃ | CH₃ | |
| 198 | —Ph | Ph | H | H | CH₃ | Ph | |
| 199 | —Ph | PhCl | H | H | CH₃ | Ph | |
| 200 | —Ph | PhCl | H | H | —CH₂CH₂CH₂CH₂— | | |
| 201 | —Ph | PhCl | H | H | CH₃ | 4-chlorophenyl | |
| 202 | —Ph | PhCl | H | H | C₂H₅ | Ph | |
| 203 | —Ph | PhCF₃ | H | H | —CH₂CH₂CH₂CH₂— | | |
| 204 | —Ph | PhCF₃ | H | H | CH₃ | 4-chloro-3-methylphenyl | |
| 205 | —Ph | PhCl₂ | H | H | i-C₃H₇ | i-C₃H₇ | |
| 206 | —Ph | PhCl₂ | H | H | —CH₂CH₂CH₂CH₂— | | |
| 207 | —PhNO₂ | Ph | H | H | H | H | HCl Salt m.p. 164–167° C. |

Most of the compounds of formula (II) can be easily prepared by the conventional methods and also some are published, for example, in the U.S. Pat. No. 2,131,362, British Patent No. 1,339,116 and British Patent No. 1,350,528.

The compound of formula (III) also can be easily prepared by the conventional methods in the art.

As described in the above, 1,3,5-thiadiazine-4-one derivatives can be easily prepared by using the compound of the present invention. For example, 1,3,5-thiazine-4-one derivatives is obtained by cycling the compound of the formula (I) in the absence of the solvent, preferably in the presence of the appropriate solvent, within a temperature range of 0° C. to 150° C., preferably 20° C. to 100° C. The reaction can be proceeded in the presence of an afore-mentioned base. The final product, 1,3,5-thiadiazine-4-one derivatives can be separated and/or purified by the conventional methods, if necessary.

Other features of the invention will become apparent in the course of the following description of the exemplary embodiments which are given for illustration of the invention and are not intended to be limiting thereof.

EXAMPLE 1

Preparation of p-nitrophenyl N-[N'-t-butyl, N"-isopropyl isothioureido] methyl-N-phenylcarbamate To a solution of 3.0 g of p-nitrophenyl N-chloromethyl N-phenylcarbamate and 1.8 g of N-isopropyl, N'-t-butyl thiourea in 30.0 ml of toluene, 3.0 g of calcium hydroxide was added and the mixture stirred at room temperature for 5 hours. The resulting product was separated by filtration and was crystallized from the mixture of hexane and ethyl acetate. 4.04 g of the product was obtained: m.p. 105°–106° C.

EXAMPLE 2

Preparation of alpha-naphthyl N-[N'-t-butyl, N"-isopropyl isothioureido]methyl-N-phenylcarbamate To 20 ml of dichloroethane, 3.0 g of alpha-naphthyl N-chloromethyl N-phenyl carbamate, 1.3 ml of triethylamine and 1.8 g of N-isopropyl N'-t-butyl thiourea was added, and the mixture was stirred at room temperature for 3 hours. The resulting mixture was washed with 20 ml of water three times and dried over sodium sulfate. Thereafter, the solution was removed, and the resulting product was crystallized from isopropyl alcohol. 3.3 g of the product was obtained: m.p. 106°–108° C.

EXAMPLE 3

Preparation of p-bromophenyl N-[N'-t-butyl, N"-isopropyl isothioureido]methyl-N-phenyl carbamate.

To 20 ml of dichloroethane, 3.4 g of p-bromophenyl N-chloromethyl-N-phenyl carbamate, 1.3 ml of triethyl amine and 1.8 g of N-isopropyl N'-t-butyl thiourea were added, and the mixture was stirred at room temperature for 1 hour. The resulting mixture was washed with 20 ml of water three times and subsequently dried over sodium sulfate. The solvent was removed and the resulting product was crystallized from isopropyl alcohol. 3.9 g of the product was obtained: m.p. 76°–78° C.

EXAMPLE 4

Preparation of methyl N-[N'-t-butyl, N"-isopropyl isothioureido]methyl-N-phenyl carbamate To 20 ml of dichloroethane, 1.9 g of methyl N-chloromethyl N'-phenyl carbamate, 1.3 ml of triethylamine and 1.8 g of N-isopropyl N'-t-butylthiourea were added and the mixture was stirred at room temperature for 1 hour. The solvent was removed, and the residue was purified by silica gel column chromatography to obtain 2.4 g of the product as liquid:

NMR(CDCl$_3$): 0.97–1.07(d,6H), 1.3(s,9H), 3.5(s,3H), 4.45–4.75 (m,1H), 5.05(s,2H), 7.3(s,5H).

EXAMPLE 5

Preparation of p-chlorophenyl N-[N'-t-butyl, N"-isopropyl isothioureido]methyl N-phenylcarbamate To 20 ml of dichloroethane, 2.9 g of p-chlorophenyl N-chloromethyl-N-phenyl carbamate, 1.3 mo of triethyl amine and 1.8 g of N-isopropyl N'-t-butylthiourea were added, and the mixture was stirred at room temperature for 1.5 hours. The resulting mixture was washed with 20 ml of water and dried over sodium sulfate. The solvent was removed, and the residue was crystallized from isopropyl alcohol to obtain 3.57 g of the titled compound: m.p. 95°–97° C.

EXAMPLE 6

Preparation of benzyl N-[N'-t-butyl, N"-isopropyl isothioureido]methyl N-phenylcarbamate To 10 ml of dichloromethane, 2.8 g of benzyl N-chloromethyl-N-phenylcarbamate and 1.5 g of N-t-butyl-N'-isopropylthiourea were added, and the mixture was stirred at room temperature for 30 minutes. Then, 1.4 ml of triethylamine was added dropwise over 5 minutes to the above mixture. After 4 hours, the mixture was washed with 20 ml of water and dried over sodium sulfate. After filtration of the mixture, the solvent was removed to obtain the orange liquid, which was purified by silica gel column chromatography to obtain 2.2 g (yield: 54%, liquid) of the product:

NMR(CDCl$_3$): 0.95–1.15(d,6H), 1.3(s, 9H), 5.0(s, 2H), 5.07(s, 2H), 7.15(s, 5H).

EXAMPLE 7

Preparation of methyl N-[N'-t-butyl, N"-isopropylisothio ureido]methyl N-2,2-dimethyl 2,3-dihydrobenzofuran-7-yl carbamate To 15 ml of dichloromethane, 1.7 g of phenyl N-chloromethyl-N-2,2-dimethyl-2,3-dihydrobenzofuran-7-yl carbamate and 0.087 g of N-t-butyl-N'-isopropyl isothiourea were added, and the mixture was stirred at room temperature for 20 minutes, to which 0.7 ml of triethylamine was added. The mixture was again stirred at the same temperature and dried over sodium sulfate. After filtration of the mixture, the solvent was removed to obtain the dark red liquid, which is subjected to silica gel column chromatography to obtain 1.3 g of the product as yellow liquid:

NMR(CDCl$_3$): 1.1–1.25(d, 6H), 1.45(s, 9H), 3.0(s, 6H), 5.05(s, 2H), 5.1(s, 2H), 6.8–7.2(m, 8H).

EXAMPLE 8

Preparation of phenyl N-[N'-t-butyl, N''-isopropyl isothioureido]methyl N-phenyl carbamate To 15 ml of dichloroethane, 2.6 g of phenyl N-chloromethyl-N-phenyl carbamate and 1.7 g of N-t-butyl-N'-isopropyl thiourea were added, and the mixture was stirred at room temperature for 20 minutes, to which 1.4 ml of triethylamine was added, and then the mixture was again stirred at the same temperature for 2 hours. The mixture was washed with 20 ml of water and dried over sodium sulfate. After filtration, the solvent was removed to obtain yellowish red liquid, which is subjected to silica gel column chromatography to obtain 2.3 g (yield: 54%) of the product:

NMR(CDCl$_3$): 1.1–1.25(d, 6H), 1.45(s, 9H), 3.0(s, 6H), 5.05(s, 2H), 5.1(s, 2H), 6.8–7.2(m, 8H).

EXAMPLE 9

Preparation of 2,2-dimethyl-2,3-dihydro-benzofuran-7-yl N-[N'-t-butyl,N''-isopropyl isothioureido]methyl N-phenyl carbamate To 15 ml of dichloroethane, 3.3 g of 2,2-dimethyl-2,3-dihydrobenzofuran-7-yl N-chloromethyl-N-phenyl carbamate and 1.7 g of N-t-butyl N'-isopropylthiourea were added, and the mixture was stirred at room temperature for 20 minutes, to which 1.5 ml of triethylamine was added and then was again stirred for 1 hour. The resulting mixture was washed with 20 ml of water, and dried over sodium sulfate. After filtration, the solvent was removed to obtain the dark red liquid, which is purified by silica gel column chromatography to form 2.5 g (yield: 53%) of the product as yellow liquid:

NMR(CDCl$_3$): 1.0–1.15(d, 6H), 1.3(s, 9H), 3.0(s, 6H), 5.0(s, 2H), 5.1(s, 2H), 6.5–7.2(m, 8H).

EXAMPLE 10

Preparation of 2-t-butylimino-3-isopropyl-5-phenyl-3,4,5,6-tetrahydro-2H-1,3,5-thiadiazine-4-one To 2 ml of dichloroethane, 4.4 g of p-nitrophenyl-N-[N'-t-butyl,N''-isopropyl isothioureido]methyl-N-phenyl carbamate and 1 ml of triethylamine were added, and the mixture was refluxed under heating for 2 hours. After cooling to room temperature, the reaction solution was washed with 20 ml of 5% aqueous sodium hydroxide solution, and subsequently washed with 20 ml of water. The resulting organic layer was dried over sodium sulfate and removed the solvent. The residue was crystallized from isopropyl alcohol to obtain 2.72 g of the final product: m.p. 103°–104° C.

EXAMPLE 11

Preparation of 2-t-butylimino-3-isopropyl-5-phenyl-3,4,5,6-tetrahydro-2H-thiadiazine-4-one To 2 ml of water and 2 ml of dichloromethane, 4.44 g of p-nitrophenyl N-[N'-t-butyl N''-isopropyl-isothioureido]methyl-N-phenyl carbamate and 0.4 g of sodium hydroxide were added, and the mixture was heated to 40° C. and stirred at the same temperature for 3 hours. After cooling to room temperature, the organic layer separated was dried and the solvent was distilled off under the reduced pressure. The residue was subjected to crystallize from the isopropyl alcohol to obtain 2.79 g of the product: m.p. 103°–104° C.

EXAMPLE 12

Preparation of 2-t-butylimino-3-isopropyl-5-phenyl-3,4,5,6-tetrahydro-2H-1,3,5-thiadiazine-4-one To a solution of 0.4 g of p-nitrophenyl N-[N'-t-butyl,-N''-isopropyl-isothioureido]methyl N-phenylcarbamate in 5 ml of acetonitrile, 0.4 g of calcium hydroxide was added, and the mixture was stirred at room temperature for 24 hours, 2.7 g of the product was prepared in the same manner as in Example 11: m.p. 103°–104° C.

EXAMPLE 13

Preparation of p-nitrophenyl N-isothioureidomethyl, N-phenyl carbamate. hydrochloride.

To 25 ml-flask, 1.16 g of p-nitrophenyl N-chloromethyl N-phenylcarbamate, 0.5 g of thiourea and 10 ml of methylene chloride were added, and the mixture was stirred at room temperature for 5 hours. The resulting white precipitates were filtered, washed with 15 ml of ethyl acetate, and dried to obtain 1.3 g of the product: 164°–167° C. (decompose).

NMR(CDCl$_3$): 5.65(s, 2H), 7.5(m, 7H), 8.28(d, 2H), 9.3(s, 2H), 9.5(s, 2H).

What is claimed is:

1. An S-(N-alkoxycarbonyl, N-substituted-)aminomethyl isothiourea derivative of the following formula:

$$R^1O-\overset{O}{\underset{\|}{C}}-\overset{R^2}{\underset{|}{N}}-\overset{R^3}{\underset{|}{CH}}-S-\overset{N-R^5}{\underset{\|}{C}}-\overset{}{\underset{|}{N}}-R^4$$
$$\phantom{R^1O-C-N-CH-S-C-N}R^6$$

wherein:
(a) R$^1$ represents an alkenyl group, an alkynyl group, a haloalkenyl group, a haloalkynyl group, an alkoxyalkyl group, a cycloalkyl group, a cycloalkenyl group, a naphthyl, a pyridyl,

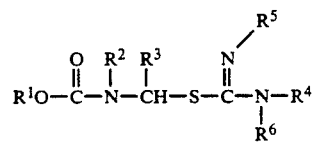

(b) each of R$^2$, R$^3$, R$^4$, R$^5$ and R$^6$, which may be the same or different, represents a lower alkyl group, an alkenyl group, an alkynyl group, a haloalkyl group, a haloalkenyl group, a haloalkynyl group, an alkoxyalkyl group, a cycloalkyl group, a cycloalkenyl group, a naphthyl, a pyridyl,

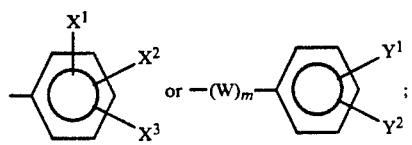

(c) each of R$^2$, R$^3$, R$^4$, R$^5$, and R$^6$ also may be a hydrogen; and (d) R⁴ and R⁵ or R⁴ and R⁶ may form —(CH₂)ₙ— (wherein n is an integer of 2 to 4), —CH₂—O—CH₂—, or —CH₂—S—CH₂—;

(e) each of X¹, X², and X³, which may be the same or different, represents a hydrogen atom, an alkyl group, a cycloalkyl group, an alkoxy group, an acetyl, a haloalkyl group, a halogen atom, CF₃, NO₂, hydroxy, a benzyl, halogen-substituted benzyl, phenyl, phenoxy or phenylthio group;

(f) each of Y¹ and Y², which may be the same or different, represents a hydrogen atom, a lower alkyl group, a halogen atom, CF₃, a lower alkoxy group;

(g) W represents a

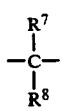

group, a —O— group, a

group, or a —OCH₂— group, and m represents an integer of 0 to 2;

(h) each of R⁷ and R⁸ represents a hydrogen atom or a lower alkyl group; provided (i) at least one of R⁴, R⁵, and R⁶ is a hydrogen.

2. The S-(N-alkoxycarbonyl, N-substituted-)aminomethyl isothiourea derivative according to claim 1 wherein R³ is hydrogen.

3. The S-(N-alkoxycarbonyl, N-substituted-)aminomethyl isothiourea derivative according to claim 1 wherein R³ is a lower alkyl group, an alkenyl group, an alkynyl group, a haloalkyl group, a haloalkenyl group, a haloalkynyl group, an alkoxyalkyl group, a cycloalkyl group, a cycloalkenyl group, a naphthyl, a pyridyl,

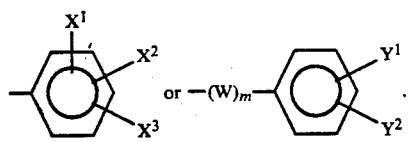

4. The S-(N-alkoxycarbonyl, N-substituted-)aminomethyl isothiourea derivative according to claim 3 wherein R³ is a naphthyl, a pyridyl,

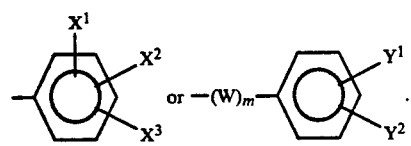

5. The S-(N-alkoxycarbonyl, N-substituted-)aminomethyl isothiourea derivative according to claim 1 wherein R² is a naphthyl, a pyridyl,

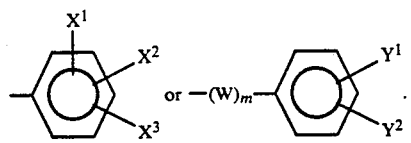

6. An S-(N-alkoxycarbonyl, N-substituted-)aminomethyl isothiourea derivative according to claim 1 wherein R⁴ and R⁵ are lower alkyl groups.

7. The S-(N-alkoxycarbonyl, N-substituted-)aminomethyl isothiourea derivative according to claim 6 wherein:

(a) R¹ and R² represents a naphthyl, a pyridyl,

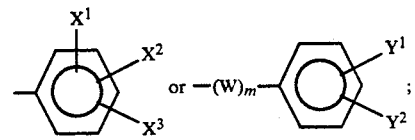

and (b) R³ is hydrogen.

8. S-(N-alkoxy carbonyl, N-substituted)amino methyl isothiourea derivative according to claim 1, which is p-nitrophenyl N-[N'-t-butyl, N"-isopropyl isothioureido]methyl-N-phenyl carbamate.

9. S-(N-alkoxy carbonyl, N-substituted)amino methyl isothiourea derivative according to claim 1, which is alpha-naphthyl N-[N'-t-butyl, N"-isopropyl isothioureido]methyl-N-phenyl carbamate.

10. S-(N-alkoxy carbonyl, N-substituted)amino methyl isothiourea derivative according to claim 1, which is p-bromophenyl N-[N'-t-butyl, N"-isopropyl isothioureido]methyl-N-phenyl carbamate.

11. S-(N-alkoxy carbonyl, N-substituted)amino methyl isothiourea derivative according to claim 1, which is p-chlorophenyl N-[N'-t-butyl, N"-isopropyl isothioureido]methyl-N-phenyl carbamate.

12. S-(N-alkoxy carbonyl, N-substituted)amino methyl isothiourea derivative according to claim 1, which is benzyl N-[N'-t-butyl, N"-isopropyl isothioureido]methyl-N-phenyl carbamate.

13. S-(N-alkoxy carbonyl, N-substituted)amino methyl isothiourea derivative according to claim 1, which is phenyl N-[N'-t-butyl, N"-isopropyl isothioureido]methyl-N-phenyl carbamate.

14. S-(N-alkoxy carbonyl, N-substituted)amino methyl isothiourea derivative according to claim 1, which is p-nitrophenyl[N-isothioureido]methyl N-phenyl carbamate.hydrochloride.

15. An S-(N-alkoxy carbonyl, N-substituted)amino methyl isothiourea derivative 2,2-dimethyl-2,3-dihydrobenzofuran-7yl N-[N'-t-butyl, N"-isopropyl isothioureido]methyl N-phenyl carbamate.

* * * * *

UNITED STATES PATENT AND TRADEMARK OFFICE
CERTIFICATE OF CORRECTION

PATENT NO. : 5,077,423

DATED : 12/31/91

INVENTOR(S) : Dae-Whang Kim et al.

It is certified that error appears in the above-identified patent and that said Letters Patent is hereby corrected as shown below:

In Column 1, line 44, delete "or" before the letter "-(W)".
In Column 1, line 65, "or" should read --to--.
In Column 15, Item 89 of the table, "n-$C_6H_{13}$" should read --n-$C_6H_{13}CH_3$--.
In Column 25, lines 10 and 11, "thiazine" should read --thiadiazine--.
In Column 26, line 22, "1.3 mo" should read --1.3 ml--.
In Column 27, line 44, "4.4" should read --4.44--.

Signed and Sealed this

Third Day of October, 1995

Attest:

BRUCE LEHMAN

Attesting Officer     Commissioner of Patents and Trademarks